United States Patent [19]

Harrison et al.

[11] Patent Number: 4,744,758

[45] Date of Patent: May 17, 1988

[54] PARTIAL DENTURE ATTACHMENT APPLIANCE

[76] Inventors: John W. Harrison, R.D. #2 Stoltz Rd., Saegertown, Pa. 16433; John H. Tucker, 809 W. 26th St., Erie, Pa. 16508

[21] Appl. No.: 41,933

[22] Filed: Apr. 24, 1987

Related U.S. Application Data

[63] Continuation-in-part of Ser. No. 710,478, Mar. 11, 1985, Pat. No. 4,661,068.

[51] Int. Cl.⁴ ............................................. A61C 13/22
[52] U.S. Cl. ..................................................... 433/181
[58] Field of Search ................ 433/181, 180, 182, 183, 433/186

[56] References Cited

U.S. PATENT DOCUMENTS

| | | | |
|---|---|---|---|
| 1,297,561 | 3/1919 | Guntner | 433/181 |
| 1,753,644 | 4/1930 | Burden | 433/181 |
| 3,344,842 | 10/1967 | Cameron | 433/181 |
| 3,955,282 | 5/1976 | McNall | 433/9 |

FOREIGN PATENT DOCUMENTS

| | | | |
|---|---|---|---|
| 500392 | 3/1928 | Fed. Rep. of Germany | 433/181 |
| 2085303 | 2/1982 | United Kingdom | 433/181 |

OTHER PUBLICATIONS

Barrick, "Recent Advances in Etched Cast Restorations", Journal of Prosthetic Dentistry, Nov. 1984, pp. 619–625.

Primary Examiner—Robert Peshock
Attorney, Agent, or Firm—Body, Vickers & Daniels

[57] ABSTRACT

An extracoronal attachment for a removable partial denture utilizes a joint comprising a fixed ball within a movable resilient tube to connect the prosthesis to the abutment teeth. The attachment is accurately constructed by a kit and applied by a method which insures that tensile and shear stresses otherwise applied to such attachments during functional loading are significantly reduced so that the male retainer may be permanently secured to the abutment teeth by means of an adhesive bond.

20 Claims, 4 Drawing Sheets

PARTIAL DENTURE ATTACHMENT APPLIANCE

This is a continuation in part of Ser. No. 710,478 filed Mar. 11, 1985 U.S. Pat. No. 4,661,068 filed Apr. 28, 1970.

BACKGROUND

This invention relates, in general, to extracoronal attachments for a removable partial denture and more particularly to the attachment and to a method and kit for use in constructing and applying such attachment.

The invention is particularly applicable to dentures having a free unilateral or bilateral end and will be described with particular reference thereto. However, it will be appreciated by those skilled in the art that the invention may have broader applications and may be applicable to other dental applications involving pontics or a bridge requiring or utilizing a joint-type attachment.

Where several posterior teeth must be replaced and the remaining teeth within the oral cavity cannot support a fixed partial denture, it is often desirable to use a removable partial denture. In order that the denture be retained in position while in use in the wearer's mouth, the partial denture must be anchored in some manner within the mouth generally by being removably attached to the abutment teeth, i.e. the anterior teeth closest to the removable bridge.

There are two basic types of anchoring attachments in use. The first type includes extracoronal attachments on a denture, such as clasps, which are used to grip around the abutment teeth. In fact, the clasps tightly grip the abutment teeth to maintain a firm connection between the partial denture and abutment teeth and while functionally acceptable, the clasps are visible and unsightly and render a particularly unsatisfactory cosmetic appearance. As an alternative to such extracoronal attachment, many different types of intracoronal and extracoronal attachments have been proposed and are in use.

One such type of extracoronal device is marketed under the commercial name "PRECI-VERTIX" which uses a male retainer attached to the abutment tooth and a female retainer embedded in the denture. More particularly, a burnout plastic male pattern in the shape of a cylindrical rod can be accurately formed and then applied to the crown pattern of the abutment tooth. The female retainer which is fitted within the denture has a slotted cylindrical opening in turn fitted with a slotted plastic, resilient sleeve to receive the male retainer to provide a precision attachment. A similar type of extracoronal attachment is marketed under the name "STERN ®JMS SYTEM" (Jacket Maintenance System) in which the female retainer is mounted within the crown of the abutment tooth and the male retainer applied to the denture. In this arrangement the full length plastic insert has a trapezoidal cross-sectional opening to receive the similarly shaped male retainer. A third extracoronal joint is marketed under the name "DALBO". In this arrangement the male retainer is attached to the abutment tooth and has a spherical ball protruding from the abutment tooth adjacent the gingival margin. The female retainer has a slotted cylindrical opening and is embedded in the denture. Within the cylindrical opening is a stiff spring which resists vertical movement of the male sphere relative to the denture. In each of the arrangements discussed, the joint formed by the male and female retainers is under significant stresses in tension and compression during normal use of the denture. This requires that one of the retainers, male or female, be securely anchored to the abutment teeth and all such attachments have heretofore required the construction of a crown over the abutment tooth. To make such a crown requires that an otherwise healthy tooth be ground down and reduced in size so that a crown containing the appropriate connected member may be cemented on the remains of the tooth to support the connected member and replace, cosmetically and functionally, the now-destroyed tooth.

Other alternative arrangements for mounting pontics have been employed which do not destroy the abutment tooth. It is known that satisfactory results have been achieved by means of a resin-bonding technique for fixed partial dentures or for a tooth replacement which is known conventionally as the Acid Etched Resin Bonded Retainer Technique. This technique, incorporated by reference herein, uses an acid etch in combination with a slight modification of the abutting teeth to resin bond the framework supporting the pontic or fixed bridge to the enamel of the abutting teeth. A close review of the retainer designs utilized with such technique disclose that the biting or functional loading forces place the retainer design primarily in compression with little tensile or shear stresses exerted on the retainer. The removable intracoronal and extracoronal precision attachments discussed above all produce significant shear and tensile stresses on the retainers which, it is believed, will not produce an acceptable, long lasting attachment, if the retainer was simply resin bonded to the abutment teeth.

SUMMARY OF THE INVENTION

It is the principal object of the invention to provide an extracoronal attachment, a method and a kit for constructing and applying the attachment to the patient's oral cavity which is generally characterized by a ball and socket joint principally under compressive loading thus permitting resin bonding of the retainer to the abutment teeth.

In accordance with one feature of the invention the general arrangement is characterized by a male retainer resin bonded to the abutment teeth and having a ball or a connecting sphere situated near the gingiva. The female retainer which is embedded within the pontic adjacent the abutment teeth has a blind slotted cylindrical opening which receives a slotted plastic sleeve whereby the denture is attached vis-a-vis the spherical joint to the male retainer. The female retainer has a flat vertically-extending face surface which is in co-planar contact with an abutment plate on the male retainer from which the connecting sphere extends. The abutment plate is in contact with the proximal wall pattern of the abutment tooth and resin bonded to the abutment teeth about an area adjacent the occlusal, proximal, and lingual surfaces of the abutment tooth. By accurately positioning the connecting sphere adjacent the mucosal tissue and maintaining parallelism of the retainers as well as providing space occlusal to the sphere, the joint is not subjected to significant tensile or shear stresses, thus permitting adhesive bonding of the male retainer.

In accordance with another feature of the invention, a kit is provided for use in the construction of the metal retainer, the insertion of the female retainer into the denture and the accurate assembly of the male-female joint. The kit includes a burnout plastic guideplane pattern and a metal female retainer housing. The plastic guideplane pattern which is burned out when the male retainer is formed by the lost wax process or similar techniques includes a generally flat abutment plate adapted to contact the proximal or posterior surface of the abutment tooth and extends vertically from its bottom end which is adapted to be positioned adjacent to the gingiva of the crown of the abutment tooth. A connecting sphere portion is positioned closely adjacent the bottom end of the abutment plate extending outwardly therefrom to establish the basic joint geometry to assure the stress loading discussed above. The metal female retainer housing has a blind tubular retaining opening and a vertically-extending slot communicating with the blind tubular opening at one end and with the vertically-extending flat forward-facing front surface of the female retainer. Also provided is a replaceable plastic insert having an outside tubular surface configured to be lockingly received within the retainer opening. The plastic insert has a cylindrical passage extending therethrough and a vertically-extending slot communicating with the cylindrical passage. A mandrel is provided for inserting the plastic sleeve into the female retainer housing with the slot in the sleeve aligned and co-planar with the slot in the retainer. To insure proper alignment of the male and female retainers during the denture construction process, the guideplane pattern is provided with buccal and lingual rails to insure the female retainer is not skewed in relation to the male retainer. To insure proper vertical positioning of the male retainer relative to the female retainer and thus avoid tensil stresses on the connecting sphere, an occlusal metal spacer is provided for insertion in the female retainer prior to taking final impressions for constructing the denture framework. A male processing member having a flat base surface similar to the guideplane pattern's abutment surface, a vertically-extending web member equal in distance to the slot depth of the plastic retainer and a cylindrical rod having a diameter equal to that of the connecting sphere is also provided. The male processing member is positioned in the master cast to permit accurate orientation of the female retainer to the male retainer and to the denture framework to insure the proper male-female retainer relationship within the oral cavity.

In accordance with another aspect of the invention, the construction of the extracoronal attachment is to some extent technique-sensitive and thus a method is provided to insure the use of proper technique for constructing the removable partial dentures. The method essentially comprises a two-step process. The first step involves the construction of the male retainer and the second step involves the construction of the denture framework with the female retainer accurately secured thereto. The method includes the necessary checks and balances to insure the accurate formation of the attachment. To construct the metal male retainer the abutment teeth are modified for occlusal or cingulum rests, an occlusal to gingival insertion path is provided and a full arch impression taken from which the master cast is prepared. The master cast is surveyed and the retainer design outlined thereon. The guideplane pattern previously described is then accurately positioned on the master cast and parallelled and a non-precious metal male retainer prepared by means of a lost wax process or the like. The retainer is modified and resin bonded to the abutment teeth. The second step of the process then comprises accurately positioning the female retainer with the plastic insert and occlusal spacer in place onto the male retainer. A lift-off impression is taken. The occlusal spacers are removed and the male processing member described above inserted into the impression. Another master cast is prepared which now contains the metal processing males. The metal processing males serve to accurately position the female retainer to the male retainer and to the framework of the removable dentures by appropriate blocking techniques utilized during the process. A comfortable and accurately fitting denture results.

It is thus an object of the invention to provide an extracoronal attachment, a method for forming a denture employing the attachment and a kit for use in the construction of the denture which results in a removable, partial denture which is (a) cosmetically appealing, (b) which uses resin bonding of the male retainer to avoid destruction of the abutment teeth, and (c) which provides a long-lasting, permanent retention of the male retainer by virtue of the lack of stresses developed within the arrangement.

It is another object of the invention to provide a method of constructing an extracoronal attachment in a removable, partial denture which ensures the accurate construction required of a precise fitting extracoronal attachment.

It is another object of the present invention to provide a relatively inexpensive and simple kit which insures the accurate positioning of the extracoronal attachment during the construction of the removable, partial denture employing such attachment.

Still other objects of the invention relate to the use of non-precious metals in an extracoronal attachment, and the use of a replaceable female sleeve member to achieve the desired, precise extracoronal attachment fit while permitting movement of the denture relative to the attachment to avoid stresses upon the extracoronal joint.

These and other objects and advantages and features of the invention will become apparent in the following description taken together with the accompanying drawings which are described in the following section.

PREFERRED EMBODIMENT

Figure 1:
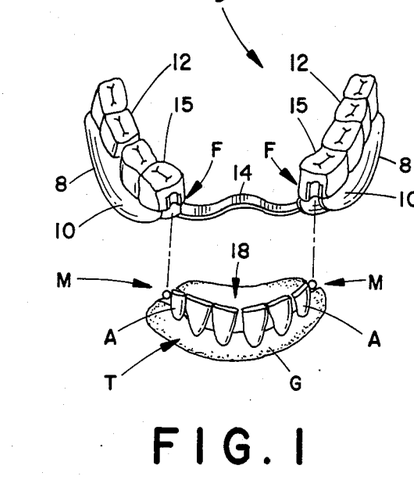
FIG. 1 is an exploded perspective view of lower natural teeth and a dental prosthesis generally illustrating a preferred embodiment of the invention and identical to that disclosed in parent application, Ser. No. 710,418, filed Mar. 11, 1985.
Figure 2:
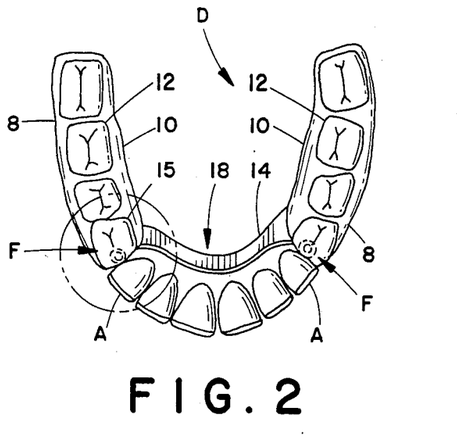
FIG. 2 is a plan view of a set of lower teeth with prostheses attached and is identical to that shown and disclosed in the parent application.

Refering now to the drawings, wherein the showings are for the purpose of illustrating a preferred embodiment of the invention only and not for the purpose of limiting the same, FIGS. 1 and 2 show a plurality of teeth T, a gingival portion of G and a removable partial denture D which is removably attached to teeth T by male retainer M on teeth T and female retainer F embedded within partial denrure D. More specifically, partial denture D shown is a mandibular bilateral free end removable partial denture. Other applications for which the extracoronal attachment disclosed herein may be applied include maxillary bilateral free end removable partial dentures, mandibular and maxillary bilateral removable partial dentures that are free on one side and have a remaining distal abutment on the other side (Kennedy Class II) and mandibular or maxillary unilateral free end partial dentures where compatible free rotation cross arch stabilization can be achieved.

Natural teeth T are embedded in the gingival portion or gingiva G of an oral cavity and are generally comprised of several adjacent teeth grouped together. For purposes of definition, the posterior tooth (teeth) to which the extracoronal device will be attached at either end of the group of teeth T is referred to as an abutment tooth (teeth) A, which will form the anchoring point for partial denture D. Depending on the denture and the type, size and condition of the natural teeth to which the denture is to be anchored, only one tooth or a plurality (as illustrated in the preferred embodiment) of natural teeth may be used to anchor the denture. Accordingly, the use of the term abutment tooth may mean abutment teeth.

Partial denture D is generally comprised to two denture portions 8, each having a saddle portion 10, denture teeth 12 and a direct retainer 14. Each side is generally similar to the other so that only one side will be discussed throughout the specifications, it being understood that the other side and attachment will be duplicated unless a unilateral free end partial denture is required. Saddle portions 10 as is well known have a generally contoured and concave seat to fit the gingival portions G of the oral cavity where the natural teeth have been removed. Denture teeth or pontics 12 are teeth substitutes simulating the original, removed teeth in form and function to as great an extent as possible and provide a denture abutment tooth or pontic 15 facing abutment tooth (teeth) A. Direct retainer 14 joins the two denture portions 8 across an interior side 18 of natural teeth T in the oral cavity, thereby forming a single unit which is too large to be swallowed by the wearer. These elements are typical of removable partial dentures.

Figure 3:
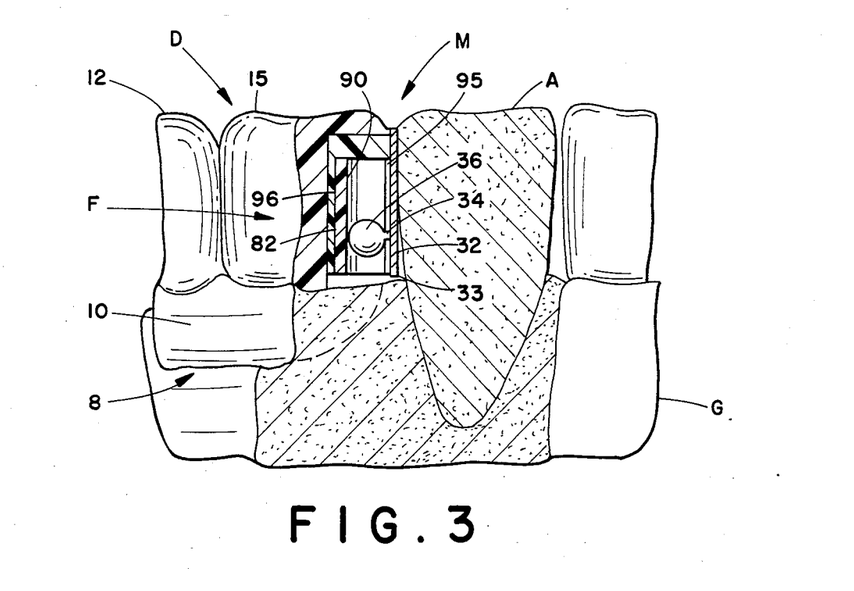
FIG. 3 is a plan view of a set of lower teeth with prostheses attached and is similar to that shown and disclosed in the parent application.

A cutaway illustrating the basic function of the assembled intracoronal attachment is shown in FIG. 3. For purposes of explaining the joint operation, male retainer M includes a vertically-extending flat abutment plate 32 which extends to the tissue or gingiva or very closely spaced therefrom at its lower end and almost to the crown occlusal portion of abutment tooth A at its upper end. Spaced closely adjacent lower end 33 of abutment plate 32 is a cylindrical or tubular shaft member 34 to which is attached a connector sphere 36. As will be explained hereafter, only the area of the proximal wall pattern of abutment teeth A in contact with the occlusal or cingulum rest and the lingual rests of the male retainer need be bonded, that is, the areas of the abutment teeth in contact with the male retainer about the upper portion of retainer teeth A. The female retainer F will be described hereafter in detail. For purposes of explaining the operation of the joint it should be sufficient to note that female retainer F has a blind, vertically-extending, slotted tubular opening 96 into which is inserted a similarly configured plastic retainer 82 which in turn has a slotted cylindrically shaped opening 90. Received snugly within cylindrical opening 90 of plastic retainer 82 is spherical connector 36. Tubular shaft member 34 of connector sphere 36 extends through the slotted opening in plastic retainer 82. Female retainer F also includes vertically-extending abutment flanges 95 which contact or rest against the outer surface of abutment plate 32. Connector sphere 36 is positioned well below the midpoint of abutment plate 32 and abutment flanges 95. The connector sphere 36 is also below the centers of pontics 12, 15 and also abutment tooth A. During functional loading the removable prosthesis will experience considerable movement. With respect to downward movement of the prostheses against the gingiva G there is sufficient space provided between connector sphere 36 and the bottom of blind opening 96 to prevent sphere 36 from "bottoming out" which would exert considerable shear stress on the male retainer. The prostheses will also tend to move in a posterior direction within the oral cavity. This movement, of course, will be resisted by connector sphere 36 which will cause a couple or a moment on the female retainer F causing the top part of female retainer F to bear against the uppermost portion of abutment plate 32 thus placing male retainer M in compression. It can thus be seen that the free space within cylindrical opening 90 between the normal position of connector sphere 36 and the bottoming out position serves a twofold function of establishing a couple to place male retainer M under compression while also avoiding any shear stress on male retainer M which might result in premature failure of the resin bond. Anterior movement of the prostheses will simply result in the abutment flanges 95 of female retainer F contacting abutment plate 32 of male retainer M to again place the male retainer M under compression at the area where it is bonded to abutment teeth A. Connector sphere 36 permits some limited skewing of the prostheses with respect to side to side and also top to bottom. On side to side skewing one of the abutment flanges 95 of female retainer F is simply unloaded while the other maintains abutment plate 32 under compression. Abutment plate 32 and abutment flange 95 tend to distribute the load uniformly over the abutment teeth A with the result that the patients receiving the extracoronal attachment described herein have commented that they do not feel any pressure on the abutment teeth even though, as noted, there is considerable movement of denture D during functional loading.

Figure 4:
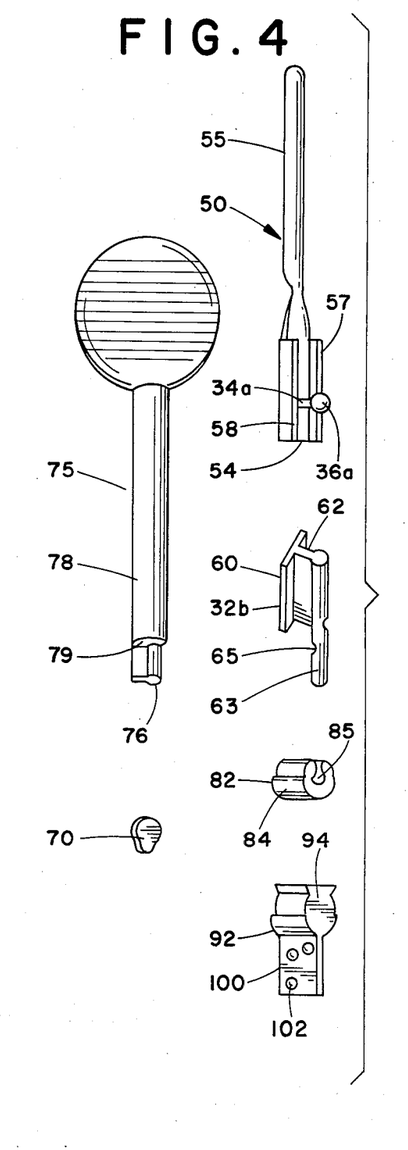
FIG. 4 is a collection of a series of perspective views showing various tools and parts necessary to construct the intracoronal attachment described herein.
Figure 5:
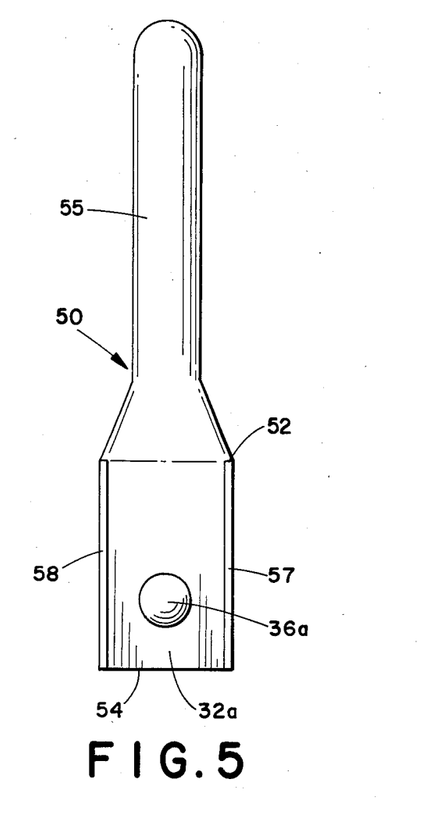
FIG. 5 is a plan view of the guideplane pattern tool shown in perspective form in FIG. 4.
Figure 6:
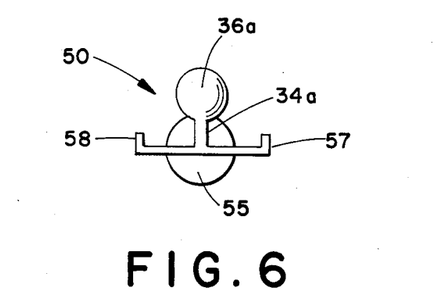
FIG. 6 is a bottom view of the guideplane pattern shown in FIG. 5.

There is shown in FIG. 4 the elements of a kit necessary to construct the intracoronal attachment described herein. As best shown in FIGS. 4, 5 and 6, one of the elements of the kit includes a guideplane pattern 50 which is made of a suitable burnout plastic material. Guideplane pattern 50 has a flat abutment plate 32(a) which has a length or extends vertically a distance sufficient to span the distance between the gingiva and the crown of any abutment tooth A. Abutment plate 32(a) has a top edge 52 adapted to be adjacent the crown of abutment tooth A and a bottom edge 54 which will be spaced closely adjacent with the gingiva G when male retainer M is formed. Extending upwardly from top edge 52 of abutment plate 32(a) is a circular handle portion 55 which is used to place guideplane pattern 50 in proper parallel, vertical relationship in the master cast. Abutment plate 32(a) extends in a lateral direction and terminates in outwardly facing lingual and buccal rails 57, 58 respectively. The rails 57, 58 extend the vertical length of abutment plate 32(a) and are used to insure proper alignment of female retainer F in a manner which will be noted hereafter. Adjacent bottom edge 54 of abutment plate 32(a) is a cylindrical shaft member 34(a) and a connector sphere 36(a). Dimensions of guideplane pattern 50 can vary depending upon the application. Dimensions of a typical guideplane pattern would include a thickness of abutment plate 32(a) of 1 mm, a length of shaft member 34(a) of approximately 2.0 mm, a connector sphere 36 radius of approximately 0.9 mm, a distance between lingual and buccal rails 57, 58 of 4.8 mm, and a vertically-extending length of abutment plate 32(a) of approximately 5.8 mm.

Figure 10:
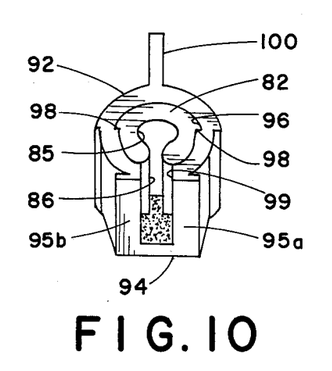
FIG. 10 is a perspective view of the bottom surface of the female retainer of the extracoronal attachment with the occlusal spacer positioned therein.
Figure 11:
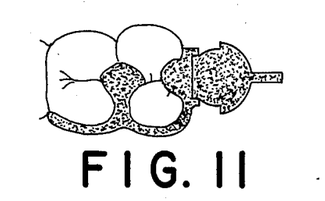
FIGS. 11 and 12 are top and side pictorial illustrarions of the female retainer applied to the male retainer.
Figure 12:
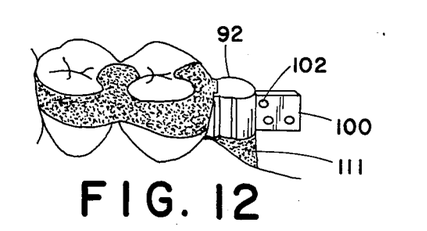

The kit also includes a metal female retainer housing 92 and a plastic sleeve or retainer 82 best shown in FIGS. 4 and 10. Female retainer housing 92 is made of a suitable alloy metal and plastic retainer 82 is made of a suitable durable perma-elastic plastic such as that supplied in extracoronal attachment kits now commercially available. Female housing 92 and plastic sleeve 82 comprise female retainer F. Female housing 92 has a closed flat top surface 94 adapted to be positioned within and closely adjacent the crown of abutment tooth A. A blind tubular opening 96 which is shown as basically horseshoe shaped extends from the bottom of female housing 92 to a point spaced from top surface 94. Tubular opening 96 is notched as at 98 to prevent movement of plastic retainer 82 therein and a vertically-extending slot 99 provides communication between tubular opening 96 and the front face of female retainer housing 92. The front face of female retainer housing 92 is defined by vertically-extending abutment flanges 95(a), 95(b) adapted to contact abutment plate 32 of male retainer M lingual and buccal flanges 95(a), 95(b) respectively which extend the full length of female retainer housing. A longitudinally-extending, flat tail member 100 defines the rearward portion of female retainer housing 92 and is ideally provided with several perforations 102 to insure secure bonding to the denture framework. Plastic retainer 82 has an outside surface 84 configured to coincide and be aligned with blind tubular opening 96 of female retainer member 92 and a length equal to the length of tubular opening 96. Plastic retainer 82 has a cylindrical opening 85 extending therethrough and is slotted as is 86 along the length thereof. Slot 86 of plastic retainer 82 is aligned with slot 99 of retainer housing 92. Cylindrical opening 85 of plastic retainer 82 has a diameter equal to that of connector sphere 36 and the distance of plastic retainer slot 86 is approximately equal to the diameter of shaft member 34.

The kit also includes an occlusal spacer 70 and a processing male 60 as shown in FIG. 4. Occlusal spacer 70 is shaped or configured in the form of cylindrical opening 85 in plastic retainer 82 and is made of a soft metal such as brass. Occlusal spacer 70 as shown in FIG. 10 is adapted to fit within cylindrical opening 85 and thus shorten the length of blind tubular opening 96 to insure the spacing between connector sphere 36 and the bottom of opening 96 as shown in FIG. 3. Processing male 60 includes an abutment plate portion 32(b) identical to abutment plate 32 of processing male M and also abutment plate 32(a) of guideplane pattern 50. Extending from abutment plate 32(b) is a web 62 which has a thickness identical to the diameter of shaft member 34 of male connector M and shaft member 34(a) of guideplane pattern 50. Secured to web portion 62 is a longitudinally-extending cylindrical rod portion 63 which has a diameter equal to that of connector sphere 36 of male retainer M and connector sphere 36(a) of guideplane pattern B. Web portion 62 extends the length of abutment plate portion 32(b) and cylindrical rod portion 63 extends beyond web portion 62 and is notched as at 65 to insure retention within the master cast as will be noted hereafter. Completing the kit is a mandrel or a seating tool 75 which has an end portion 76 configured in the shape of occlusal spacer 70 and cylindrical opening 85 of plastic retainer 82. End portion 76 extends a distance not greater than the length of blind tubular opening 96 and terminates at a cylindrical rod portion 78 so that the intersection of the end portion 76 and rod portion 78 defines a circular abutment surface 79. End portion 76 is used to seat occlusal spacer 70 within plastic retainer 82 and abutment surface 79 is used to seat plastic retainer 82 within tubular opening 96 of female metal housing 92.

Reference will now be made to FIGS. 7 through 16 for a description of the method of forming the male retainer M and securing the female retainer F within the prosthesis. In the description reference will be made to several processing steps involving casting and molding and various procedures used in the casting and molding process. All such steps and processes are well known and conventionally practiced in the dental art and will not be described in any significant detail herein.

The process is essentially a two step process involving first the formation of the male retainer M and then the insertion of female retainer F with appropriate checks built into the process to insure that the partial denture D is formed in the precise geometrical relationship required for a precision intracoronal attachment.

Several preliminary steps are first required to determine whether or not the extracoronal attachment described herein is suitable for application to the particular case under study. Generally, there must be an incisal/occlusal to gingival path of insertion for the retainer. The abutment teeth must also be able to sustain a distal/occlusal rest or cingulum rest of the male retainer M. There must be sufficient tooth enamel for acid etching and bonding the rests and the abutment tooth must have an intra-occlusal space of 3.5 mm. Initially, preliminary impressions are taken and study casts are obtained from the impressions in a known manner. The study casts are mounted on a surveyor (such as shown in U.S. Pat. No. 3,344,842) to determine the heights of contour of the abutment teeth. Plans are then made to modify abutment teeth A to establish an occlusal/gingival path of insertion, create occlusal or cingulum rest seats and to create as broad a surface area as possible for bonding of male retainer M. At this time, splinting of peridontally weakened teeth can be considered. The abutment teeth are then modified by grooving or removing portions of the enamel to establish the occlusal to gingival path of insertion of the retainer and to prepare distal occlusal or cingulum rest seats. Reference may be had to an article entitled "Recent Advances in Etched Cast Restorations" by Gerald Barrack, D.D.S. appearing in the November 1984 issue of *Prosthetic Dentistry* at page 619 which describes preparation of abutment teeth for insertion of a fixed partial denture by resin bonding (incorporated herein by reference). The cingulum rest seats prepared in accordance with the invention described herein, ideally should be deeper and more pronounced than that used in fixed bonded restorations of the type disclosed in the Barrack article. Alternatively a mesial occlusal rest can be used. In certain applications an alternative to a deeper, more pronounced rest is an incisal rest which would be used only to secure proper positioning of male retainer M. The incisal rest would be removed after male retainer M was bonded to the abutment teeth.

Figure 7:
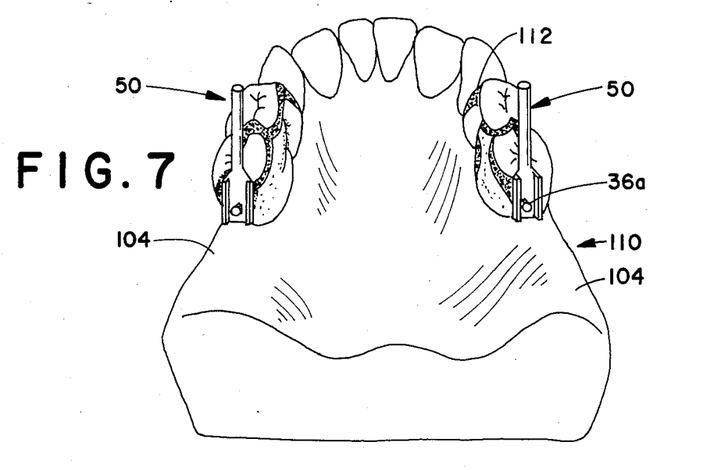
FIG. 7 is a perspective view of the guideplane pattern with the male retainer abutment portion secured to a master cast prior to forming the male retainer of the extracoronal attachment.
Figure 8:
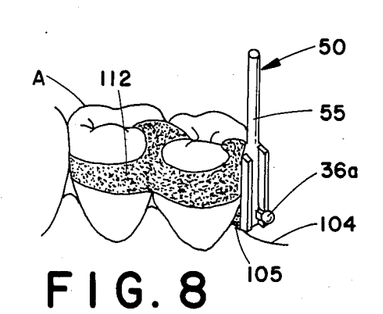
FIG. 8 is another perspective view showing the guideplane pattern attached to the abutment teeth but viewed from a different angle than that shown in FIG. 7.

After the abutment teeth have been modified as noted above, an accurate full arch final impression is taken and an appropriate master cast is prepared therefrom in accordance with conventional techniques. The master cast can be poured in die stone or alternatively a refractory material may be used if a casting divestment technique is selected to fabricate male retainers M. The master cast shown as 110 in FIG. 7 is placed on a surveying table (not shown) and the retainer design or more specifically the retainer patterns (shown as the shaded areas designated by number 112 in FIGS. 7 and 8) are fabricated out of wax or hard curing pattern resin in accordance with conventional techniques. It is now necessary to correctly position guideplane patterns 50 to retainer patterns 112. More particularly, as best shown in FIG. 7, connecting spheres 36(a) are positioned over the crest 104 of the jawbone ridge and a surveyor is used to orientate the lingual and buccal rails 57, 58 to be generally normal to the ridge 104. More importantly, rails 57, 58 of both guideplane patterns 50 are orientated to be parallel to one another. As shown in FIGS. 7 and 8 the vertical position of guideplane pattern 50 is such as to position the bottom edge 54 of abutment plate 32 as close to crest 104 as possible without permitting connector sphere 36(a) to contact crest 104 of the jawbone ridge. Connector sphere 36(a) must be positioned far enough below the occlusal plane of abutment teeth A to provide enough space for metal female retainer 92 movement. Further, if there is some exposed cementum on the proximal surface of abutment tooth A, an embrasure space such as shown at 105 in FIG. 8 must be created since it is not possible to bond tooth cementum. Embrasure space 105 will permit easy cleaning and maintenance of periodontal health.

With guideplane patterns thus positioned on the master cast and the retainer patterns 112 thus formed male retainer M can be invested and cast in a non-precious alloy in a conventional manner. A nickel beryllium metal containing non-precious alloy is recommended for strength and its properties.

Figure 9:
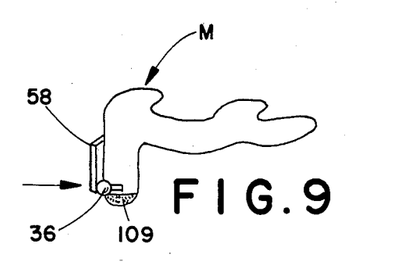
FIG. 9 is a plan view of the male retainer of the intracoronal attachment in an "as cast form"

The cast metal retainer M is polished and finished as shown in FIG. 9. More particularly, lingual rail is ground away leaving only buccal rail 58 for guide purposes as shown and the gingival of the proximal plate is now reduced and rounded off for proper gingival contour and contact much like that of a pontic. The reduced area below connecting sphere 36 is indicated by the arrow and the shaded portion shown as 109 in FIG. 9. During the polishing and finishing operation of male retainer M, care is to be taken to avoid any contact with connector sphere 36.

Cast retainers M are then tried in the patient's mouth to insure proper fit and when fit is insured the retainers may be returned to the laboratory for etching or they may be etched on the site and resin bonded to abutment teeth A in the conventional known manner. This method is explained in the Acid Etched Resin Bonded Retainer Technique noted above. It essentially involves chemically etching retainer M and applying a 30-40% phosphoric acid solution to etch abutment teeth A followed by water rinse and air drying. An enamel bonding agent, generally comprised of a combination of an unfilled and filled resin is then employed to cement male retainer M to abutment teeth A. A conventional rubber dam isolation technique should be used when bonding male rerainer M.

With the first step completed, the process continues to the second step of properly positioning female retainer F to denture D in proper relationship to male retainer M. Mandrel 75 is used to insert plastic retainer 82 into female retainer 92 and then occlusal spacer 70 is inserted into the bottom of plastic retainer cylindrical opening 85. Female retainer 92 is then mated with male retainer M with the buccal rail 58 maintaining the attitude of female retainer 92 in its proper position and the occlusal spacer 70 maintaining female retainer 92 at the proper height in relation to the position of connector sphere 36. Prior to making the final impression of the oral cavity, the area between the tissue and the bottom of female retainer 92 including embrasure space 105 is blocked out using conventional material available for that purpose as indicated by the shaded area shown at 111 in FIG. 12. Importantly, the blocked out material does not extend into any area between the tissue and the tail portion 100 of female retainer 92. A final accurate full arch impression is then made from any accurate impression material which is capable of picking up or withdrawing female retainers 92. Because female retainers 92 are to be withdrawn in the impression, reversible or irreversible hydrocolloid is not recommended for use as the impression material since it tears too easily.

Figure 13A:
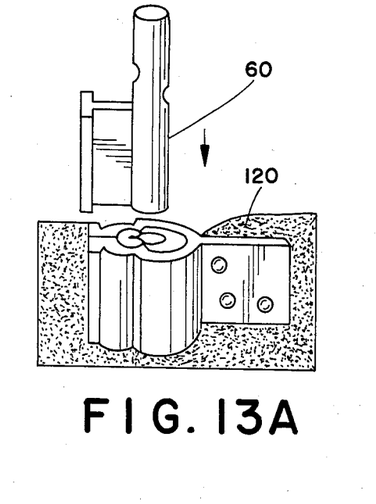
FIGS. 13(a) and 13(b) are pictorial illustrations of the male processing member being inserted into the female retainer embedded within an impression.
Figure 13B:
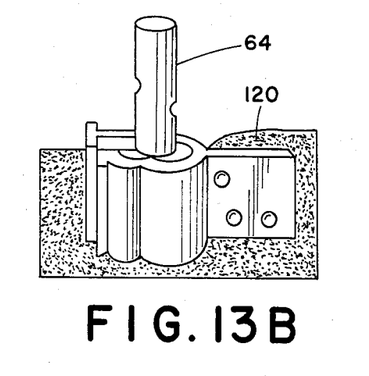
Figure 14:
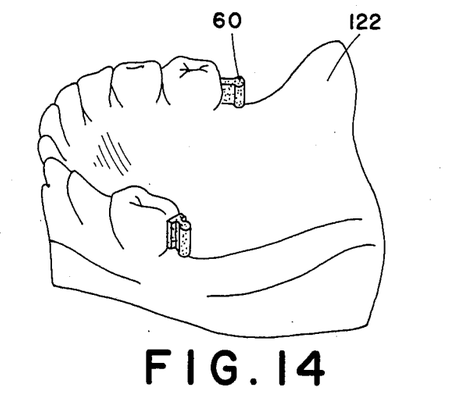
FIG. 14 is a view of the master cast with the male pocessing members positioned thereon.
Figure 15:
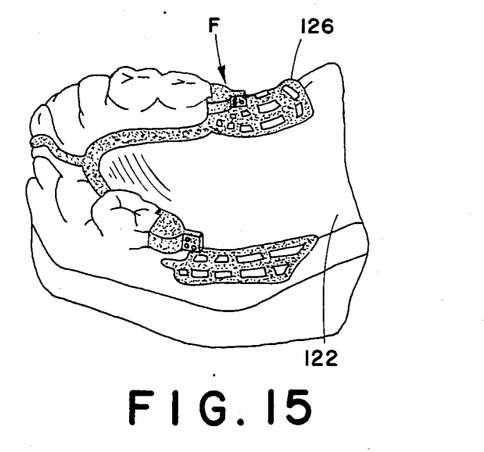
FIG. 15 is a perspective view of the master cast showing the dental framework with the female retainer secured thereto.
Figure 16:
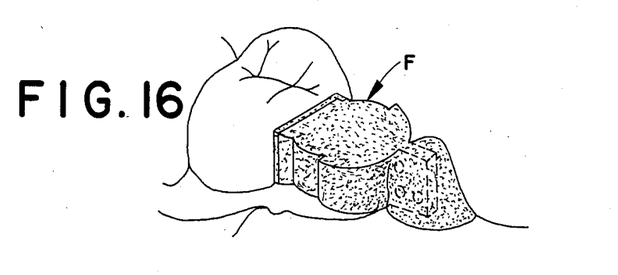
FIG. 16 is a more detailed perspective view showing the tail of the female retainer secured to the denture framework.

At this point occlusal spacers 70 are removed from female retainers 92 which are embedded in the impression material, the impression material being shown by the shaded area 120 in FIGS. 13(a) and 13(b). Processing males 60 are inserted into the impression through the bottom end of female retainers 92. A master cast is then made from the impression and the tail portion 64 of processing males 60 will be embedded in and properly orientate processing males 60 in the final master cast which is shown as 122 in FIG. 14. Processing males 60 are thus orientated in master cast 122 in their proper parallel relationship and also provide the appropriate occlusal spacing required above connecting sphere 36. Female retainers 92 with plastic inserts 82 are now recovered from the impression and reseated on processing males 60. With the female retainers F in position on processing males 60, all undercuts are blocked out in master cast 122 which is prepared for refractory duplication by pre-relieving tissue bearing areas, creating tissue stops etc. An accurate refractory cast is poured and an appropriate partial dental framework 126 is then waxed, invested, cast and finished using the refractory cast in accordance with conventional procedures (not shown). Partial denture framework 126 is then seated on master cast 122 as shown in FIG. 15 and joined as shown in FIG. 16 to female retainer F. This can be done by soldering or by using autopolymerizing acrylic resin. The use of resin is recommended as it provides for easier reassembly in the patient's mouth, if framework 126, for any reason, does not fully seat.

Female retainer F with denture framework 126 is then fitted in the patient's mouth and once a satisfactory fit has been established, the remaining buccal rail 58 on metal retainer M is removed such as by use of a cylindrical diamond attachment and a high speed drill. The remainder of denture D is then formed in accordance with conventional normal practice. When the denture D is fitted occlusal spacers 70 are again attached to female retainers F but after fitting, occlusal spacers 70 are removed.

The construction procedure described has been set forth to cover the complete construction of a removable partial denture. The extracoronal attachment described can be applied to existing removable partial dentures, especially those using extracoronal clasp retention. In such a conversion the male retainer is bonded to the abutment teeth in the first step as described above. However, the female retainer is modified to fit within the space of the existing denture abutment tooth and the existing clasp with the original dentures are used to precisely position female retainer 92 within the existing denture. Also, while the extracoronal attachment has been designed for resin bonding, the male retainer M can be applied to conventional cast crowns in the normal manner, since the attachment shown herein possesses certain advantages which justify its use over other extracoronal attachments.

A number of observations have been noted after applying the invention to a number of cases. All patients have remarked that they were aware of considerable movement of the removable prostheses during functional loading but that they did not feel any pressure on abutment teeth A. In addition, a minimal amount of office time is required to construct the removable partial denture described herein. Resin bonding male retainers M minimize tooth preparation time and greatly conserves healthy tooth structure. No temparization is required when bonded retainers are used. Male retainers M may be used with the conventional cast crowns. There definitely appears to be less force exerted on male retainer M than that of a retainer for a conventional fixed prostheses. Servicing the extracoronal attachment is easy since there are no moving parts. If retention is decreased due to wear of plastic retainer 82, a new plastic retainer 82 can be inserted in much less than a minute and the attachment can not be over adjusted. The relatively small size of the extracoronal attachment described herein permits application in as little as 3.5 mm of vertical space. The design of the attachment allows for maintenance of good oral hygiene and also provides the patient with a device which has an easy, non-critical parh of insertion. The cost of constructing the male and female retainers M, F is significantly reduced when compared to other methods and the attachment provides for improved esthetics and comfort over conventional clasp-retained prostheses. Finally, the process described is reversible and abutment tooth A remains intact.

It is thus the essence of our invention to provide an extracoronal attachment, a method for applying the attachment to a removable partial denture and a kit for use in the method, all of which results from a male-female joint arrangement which reduces the tensile and shear stress on the retainer to permit the retainer to be resin bonded to the abutment tooth as well as being applied to conventional cast crown arrangements.

Having thus described the invention, the following is claimed:

1. A method for constructing and applying at least one non-clasp retained, removable partial denture without crowns comprising the steps of:
   (a) modifying the enamel about the posterior surface of a retaining abutment tooth to create a flat broad surface adjacent the occlusal surface thereof for placement of a spherical metal male retainer having a flat base surface thereagainst;
   (b) preparing a cast from a full arch impression of the jaw receiving said denture after modifying said abutment tooth;
   (c) providing a guideplane pattern having a flat, vertically-extending abutment plate portion and a connector sphere spaced slightly from one end of said abutment plate portion and extending outwardly therefrom;
   (d) surveying and positioning said guideplane pattern with said sphere centered over the crest of the jawbone ridge, said abutment plate portion extending generally normal to said ridge, said sphere spaced away from the occlusal surface of said abutment tooth and closely adjacent the tissue of said jawbone;
   (e) forming said male retainer out of metal from said guideplane pattern by the use of the lost wax process and the like;
   (f) etching said male retainer;
   (g) bonding said vertically-extending base surface of said male retainer to the enamel of said posterior surface of said abutment tooth in an area adjacent the occlusal surface of said abutment tooth by means of an adhesive resin;
   (h) providing a metal female retainer member having a blind vertically-extending opening from the bottom thereof, a resiliant insert having a cylindrical opening extending therethrough, said insert within said blind opening, said insert and said female retainer having a vertically-extending groove communicating with said openings;
   (i) forming a removable denture;
   (j) securing said female retainer within the anterior pontic of said denture;
   (k) seating said denture by positioning said connector sphere within said groove of said plastic insert.

2. The method of claim 1 wherein said method is applicable to mandibular and maxillary bilateral removable partial dentures, a second guideplane pattern is provided in step (c) and said first and second guideplanes are positioned parallel to one another in step (d).

3. The method of claim 1 further including preparing lingual, cingulum reliefs in the enamel of the abutment tooth in step (a) so that the male retainer when formed in step (e) has cingulum rests for said abutment tooth.

4. The method of claim 3 wherein said cingulum reliefs are also formed in the tooth adjacent said abutment tooth.

5. The method of claim 3 further including the step of providing said guideplane pattern with lingual and buccal vertically-extending stabilizing rails and the step of grinding one of said rails flush with said base surface after said male retainer has been formed but prior to said etching step.

6. The method of claim 5 further including the step of grinding the gingival portion of said male retainer so as to resemble a pontic prior to etching said male retainer.

7. The method of claim 1 further including the step of positioning said sphere of said guideplane as close to said ridge without contacting said ridge as possible.

8. The method of claim 1 further including the steps of providing a metal occlusal spacer conforming in shape to the cylindrical opening and groove of said plastic insert of said female retainer and of a predetermined length; inserting said occlusal insert into said plastic insert of said female retainer; attaching said female retainer with said occlusal insert to said male retainer after said male retainer is bonded to said abutment; preparing a full arch final impression of the jaw by means of a conventional process; removing said occlusal spacer from said female retainer; providing a metal processing male member having a flat base surface identical to said abutment plate portion of said guideframe pattern, a vertically-extending cylindrical rod portion parallel to said base surface of said processing male member, said rod having a diameter equal to said sphere of said guideplane pattern and spaced from said flat space surface the same distance said sphere is spaced from said abutment plate; inserting said male processing member into said female retainer in said impression; pouring a master cast of said impression, said master cast containing said male processing member orientated within said cast in the identical position said male retainer is orientated relative to said abutment tooth.

9. The method of claim 8 further including the steps of providing said female retainer with a tail portion: inserting said female retainer on said processing male member in said master cast; blocking out undercut areas between said tail portion and the jaw portion of said cast, duplicating said master cast after said blocking step in a refractory material; waxing, investing, casting and finishing the removable partial denture framework from said duplicating cast; seating said framework on said master cast; securing said tail end of said female retainer member to said framework.

10. The method of claim 9 further including the additional step of grinding said buccal rail flush with said abutment plate of said male retainer after securing said female retainer to said denture framework.

11. A kit for providing a permanent extracoronal attachment for use in constructing removable, partial dentures with unilateral or bilateral free ends, said attachment comprising a male retainer bonded to the enamel of an abutment tooth, said kit comprising:

(a) a plastic guideplane pattern for use in constructing by the lost wax process and the like, a ball shaped, male extracoronal attachment, said guideplane pattern including a generally flat abutment plate adapted to contact the posterior surface of said abutment tooth and extending vertically from a bottom end adjacent the gingival to a top end adjacent the occlusal surface of said abutment tooth, a spherical ball spaced closely adjacent said bottom end of said abutment plate and extending outwardly therefrom;

(b) a metal female retainer having a blind tubular retainer opening therein from the bottom surface thereof, a vertically-extending slot communicating with said opening;

(c) a replaceable insert having an outside tubular surface configured to be lockingly received within said retainer opening, said insert having a cylindrical opening therethrough and a vertically-extending slot communicating with said cylindrical passage, said vertically-extending slot in said plastic insert adapted to be aligned and co-planar with said slot in said retainer.

12. The kit of claim 11 wherein said flat abutment plate has a vertically-extending rail at its lingual edge and a similar vertically-extending rail at its buccal edge.

13. The kit of claim 12 wherein said sphere of said guideplane has a radius of approximately 0.9 mm, said guideplane having a tubular member approximately 2.0 mm in length connecting said sphere to said abutment plate.

14. The kit of claim 13 further including an occlusal insert spacer having a tubular configuration similar to the configuration of said cylindrical opening and said slot formed in said plastic insert, said insert spacer adapted to fit into said female retainer and extend from a position adjacent the crown of said abutment tooth to a distance spaced from the gingival margin of said abutment tooth to insure that said retainer's spherical ball is positioned closely adjacent to but not in contact with the tissue of said jawbone.

15. The kit of claim 14 wherein said occlusal insert spacer is a brass insert.

16. The kit of claim 14 further including a metal male processing member, said member having a flat base surface similar to said flat abutment surface of said plastic guideplane pattern, a vertically-extending web member equal in width to said slot of said plastic retainer, a cylindrical rod having a diameter equal to said cylindrical opening of said plastic retainer, said male processing member adapted to fit into said plastic retainer when said female retainer has been removed from an impression for constructing a master cast whereby said female retainer and said denture may be accurately positioned thereon.

17. The kit of claim 14 further including a mandrel for inserting said plastic retaining sleeve into said female retainer housing and said occlusal spacer insert into said plastic retainer sleeve.

18. An intracoronal attachment comprising a male retainer bonded to the enamel of at least one abutment tooth and a female retainer embedded in a removable, partial denture, said male retainer comprising a flat abutment plate portion having a top end adjacent the occlusal surface of said abutment tooth and a bottom end adjacent the gingival, a tubular shaft positioned in the center of said abutment plate adjacent said bottom end and extending away from said abutment plate, a connecting sphere secured to the end of said shaft;

said female retainer comprising a retainer housing having a closed top end adapted to be adjacent said top end of said abutment plate and a bottom end having a blind tubular opening extending therein, a flat front face surface adapted to be in contact with said abutment plate, said front face surface defined by a slotted groove communicating with said tubular opening over the length thereof and buccal and lingual bearing surfaces on each side of said slotted surface;

a plastic retainer positioned in a non-rotatable manner within said tubular opening, said retainer having a cylindrical opening and a slot extending the length thereof aligned and co-planar with said slotted groove of said retainer;

said shaft member extending through said slot, said connecting sphere firmly engaged within said cylindrical opening of said plastic retainer adjacent said bottom end of said female retainer, and removed from said occlusal surface of said abutment tooth;

said abutment plate adhesively bonded to the said abutment tooth about an area of said abutment tooth adjacent the occlusal surface of said abutment tooth.

19. The attachment of claim 18 wherein said male retainer includes lingual retainer arm, occlusal and/or cingulum rests on said abutment tooth.

20. The attachment of claim 18 wherein said connecting sphere is positioned below the midpoint of the distance from the gingival to the occlusal surface of said abutment tooth.

* * * * *